United States Patent
Son

(10) Patent No.: US 10,661,054 B2
(45) Date of Patent: May 26, 2020

(54) DEVICES AND RELATED METHODS FOR URINARY CATHETERIZATION

(71) Applicant: Kenneth A. Son, Fernandina Beach, FL (US)

(72) Inventor: Kenneth A. Son, Fernandina Beach, FL (US)

( * ) Notice: Subject to any disclaimer, the term of this patent is extended or adjusted under 35 U.S.C. 154(b) by 54 days.

(21) Appl. No.: 15/271,215

(22) Filed: Sep. 20, 2016

(65) Prior Publication Data
US 2018/0078736 A1    Mar. 22, 2018

(51) Int. Cl.
*A61M 25/00* (2006.01)
*A61M 27/00* (2006.01)

(52) U.S. Cl.
CPC ........ *A61M 25/0068* (2013.01); *A61M 27/00* (2013.01); *A61M 25/0041* (2013.01); *A61M 2025/0008* (2013.01); *A61M 2202/0496* (2013.01); *A61M 2210/167* (2013.01)

(58) Field of Classification Search
CPC .......... A61M 25/0097; A61M 25/0068; A61M 25/0069; A61M 25/0136; A61F 2002/047
See application file for complete search history.

(56) References Cited

U.S. PATENT DOCUMENTS

| | | | | |
|---|---|---|---|---|
| 2,211,975 A | * | 8/1940 | Hendrickson | A61M 25/005 138/118 |
| 4,068,659 A | * | 1/1978 | Moorehead | A61M 25/0014 604/159 |
| 5,427,115 A | * | 6/1995 | Rowland | A61B 10/04 600/569 |
| 5,919,170 A | * | 7/1999 | Woessner | A61M 25/0108 604/264 |
| 6,027,462 A | * | 2/2000 | Greene | A61M 25/0136 600/585 |
| 6,358,229 B1 | * | 3/2002 | Tihon | A61M 25/0017 604/164.01 |
| 8,998,882 B2 | * | 4/2015 | Knapp | A61M 25/002 604/317 |
| 2005/0090779 A1 | * | 4/2005 | Osypka | A61M 25/0097 604/160 |
| 2007/0244423 A1 | * | 10/2007 | Zumeris | A61M 25/0017 604/22 |
| 2009/0306540 A1 | * | 12/2009 | Williams, III | A61B 10/0291 600/562 |
| 2012/0165791 A1 | * | 6/2012 | Lovmar | A61M 25/0017 604/544 |

OTHER PUBLICATIONS

Talbot, Kay et al., Catheter Care Guidelines, 2006.*
http://www.medtechga.com/video-how-to-use-instant-cath-coude-tip-catheters, Published May 24, 2017, MTG Catheters Medical Technologies of Georgia.

* cited by examiner

*Primary Examiner* — Nathan R Price
*Assistant Examiner* — Melissa A Snyder
(74) *Attorney, Agent, or Firm* — Capitol Patent & Trademark Law Firm, PLLC

(57) ABSTRACT

A Coude catheter insures proper drainage and reduces tissue damage by using an alignment indication section having an open passageway positioned on a proximal end of the catheter.

15 Claims, 3 Drawing Sheets

DEVICES AND RELATED METHODS FOR URINARY CATHETERIZATION

Coude catheters are used to drain fluid from the bladder of an individual. A typical Coude catheter is an elongated, hollow tube device made of silicon, for example, that has a shaped curve on one end. The end with the curve (the "distal end") is typically inserted into an individual's urethra, until it reaches the bladder. Prior to reaching the bladder the catheter must pass through a portion of the urethra that passes through the prostate of the individual ("prostatic urethra portion").

In the case where the individual's prostate is enlarged, the prostate may press upon the urethra, causing the prostatic urethra portion to narrow or even close (i.e., an obstruction). In either case, the individual's bladder may not be able to drain properly. To relieve the bladder, a catheter must pass through the obstructed or narrowed prostatic urethra portion.

Accordingly, in existing Coude catheters the distal end of such a catheter is shaped (i.e., curved) to advantageously pass within, and through, the prostatic urethra portion even if it has been narrowed or obstructed.

Though the distal, curved end permits existing Coude catheters to effectively pass through an individual's prostatic urethra, to effectively remove material from the bladder requires an additional step. More particularly, upon reaching the prostatic urethra the curved, distal end must be positioned in the correct spatial plane.

Unfortunately, existing Coude catheters are not designed to provide an individual (e.g. a patient) or a health care provider with an indication as to what position (i.e., what plane) the distal, curved end of the catheter is in after the catheter is inserted into an individual's urethra and reaches the individual's prostate.

In the event that a given individual has an enlarged prostate or a bladder neck contracture, catheterizations are very difficult using existing Coude catheters, and many times, lead to complications. In the future, both patients and medical extenders will be required to provide an increased level of care than in previous years. This will lead to an increased number of complications using existing catheters.

The present inventor, after thirty years of urology practice, has realized that a solution is needed to overcome the inherent limitations of existing Coude catheters.

More particularly, there is a need for a Coude catheter that provides an individual (e.g., patient or care-giver) with a proper indication that the catheter is positioned correctly, while at the same time providing the individual with a way to easily adjust the position of a catheter so that it is positioned correctly.

SUMMARY

Figure 1A:
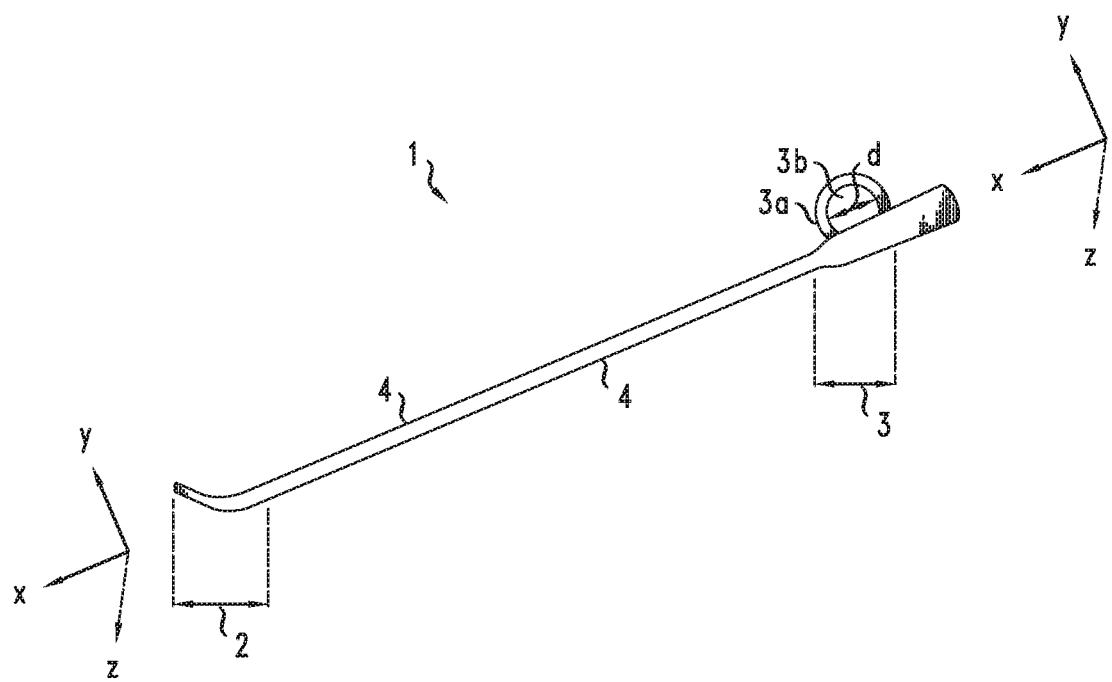
FIG. 1A depicts a rendering of a catheter according to an embodiment of the invention.

Accordingly, the inventor provides inventive methods and devices to address the shortcomings of existing catheters.

In one embodiment, an inventive catheter may comprise: (i) a curved section on one end of the catheter, (ii) an alignment indication section comprising an open passageway on another end of the catheter and configured substantially within a same spatial plane as the curved section, and (iii) a lumen section between the curved section and the alignment indication section. The curved section may comprise a Coude curved section.

In one embodiment the curve section, alignment indication section and lumen section may comprise an integrated, one-piece catheter while in another embodiment the catheter may comprise more than one component (e.g., a separate alignment section that is connected to or otherwise attached to combined lumen and curved sections).

In various embodiments the catheter may be made from a silicon or polyvinyl chloride material.

The alignment indication section may be configured or shaped in a number of different ways. In one embodiment the alignment indication section may be configured as a loop at a proximal end of the catheter, while the curved section may be configured at a distal end of the catheter.

The size of the open passageway may vary to allow different size fingers or a manipulative device to fit within the passageway. In one embodiment, the diameter of the passageway may be approximately 1.9 millimeters. That said, it should be understood that the open passageway may comprise an adjustable passageway or section whose diameter may be adjusted to account for the size of a particular individual's fingers or the size of a manipulative device.

On another embodiment the alignment indication section may comprise a compressible top portion, or no top portion at all. Still further, the alignment indication section may comprise one or more indentations on an inside or outside circumferential surface to permit an individual to better grip or hold such a section.

In another embodiment, instead of configuring the alignment indication section and its open passageway within the same spatial plane as the curved section, an alternative catheter includes an alignment indication section that is configured in a different spatial plane as the curved section. Of course, such a catheter also includes a lumen section between the curved section and the alignment indication section as well as a curved section on an end (i.e., distal end) opposite the alignment indication section (i.e., proximal end). This alternative catheter configuration may also include a compressible top portion as a part of the alignment indication section, or no top portion at all. Still further, the alignment indication section may comprise one or more indentations on an inside or outside circumferential surface to permit an individual to better grip or hold such a section Besides the catheters described above and herein, the inventor also provides catheterization methods, including one method that comprises inserting a Coude, curved section on a distal end of the catheter into an individual's urethra, and positioning an alignment indication section comprising an open passageway on a proximal end of the catheter to allow proper drainage from the individual's bladder.

Prior to inserting the catheter, the method may further comprises attaching the alignment indication section comprising the open passageway on the proximal end of the catheter.

In any event, the method orientates the curved section anteriorly with respect to a patient in a supine position using the alignment indication section.

DETAILED DESCRIPTION

Exemplary embodiments of inventive catheters (e.g., Coude catheters) and their use are described herein and are shown by way of example in the drawings. Throughout the following description and drawings, like reference numbers/characters refer to like elements.

It should be understood that, although specific exemplary embodiments are discussed herein, there is no intent to limit the scope of the present invention to such embodiments. To the contrary, it should be understood that the exemplary embodiments discussed herein are for illustrative purposes, and that modified and alternative embodiments may be implemented without departing from the scope of the present invention.

It should also be noted that one or more exemplary embodiments may be described as a process or method. Although a process/method may be described as sequential, it should be understood that such a process/method may be performed in parallel, concurrently or simultaneously. In addition, the order of each step within a process/method may be re-arranged. A process/method may be terminated when completed, and may also include additional steps not included in a description of the process/method.

As used herein, the term "and/or" includes any and all combinations of one or more of the associated listed items. As used herein, the singular forms "a," "an" and "the" are intended to include the plural form, unless the context and/or common sense indicates otherwise.

It should be understood that when a component or element of an inventive catheter is referred to, or shown in a figure, as being "connected" to (or other tenses of connected) another component or element such components or elements can be integrally and directly connected, or may use intervening components or elements to aid a connection. In the latter case, if the intervening components and elements are well known to those in the art they may not be described herein.

When the words "first" or "second" or other similar words denoting a number are used it should be understood that the use of these words does not denote a level of importance or priority. Rather, such words are used to merely distinguish one section or component of an inventive catheter and/or its position from another section or component and/or its position.

As used herein, the term "embodiment" refers to an example of the present invention.

The most likely users of Coude catheters, but by no means the exclusive users, are those individuals that are elderly. Many elderly users suffer from decreased manual dexterity and failing eyesight. Thus, in developing the inventive Coude catheters described herein the present inventor kept these considerations in mind. Yet further, the present inventor considered the importance of insuring that the inventive catheters provide an indication of the present position of the catheter both during, and after, insertion.

Still further, the inventor realized that a simple directional indicator would not suffice because of the need to adjust the catheter (i.e., simply indicating the catheter is presently out of position is not enough; a method must be provided to adjust the catheter so that it is in the proper position).

In more detail, the inventor recognized that an inventive catheter should provide its user with the ability to adjust the catheter to ensure that the catheter is positioned in a correct spatial plane.

Accordingly, the inventor discovered that including an inventive alignment indication section having an open passageway (e.g. a loop) on the proximal end of a Coude catheter provided an acceptable method for both indicating the present position of the catheter and adjusting the present position of the catheter (if need be) to a correct position (i.e., in the correct spatial plane) to permit proper drainage of material from the user's bladder (i.e., properly aligning the catheter to allow proper drainage).

Referring now to FIG. 1A, there is depicted a catheter 1 (e.g., Coude catheter) according to one embodiment of the invention. As shown in FIG. 1A, the inventive catheter 1 comprises a Coude curve section 2, an alignment indication section 3 having an open passageway 3b with a diameter "d" and a lumen section 4. In the embodiment depicted in FIG. 1A the alignment indication section 3 is shaped as a loop, though this is just one of the many shapes such a section may take.

In the embodiment depicted in FIG. 1A, sections 2 through 4 comprise an integrated, one-piece catheter manufactured from the same or similar material, such as silicon or polyvinyl chloride, for example. In an alternative embodiment, the section 3 may be a separate component that can be attached to the lumen section 4 of the catheter 1, for example, by attachment means that are known in the art (e.g., snap-on connections, threaded connections, mated, non-threaded connections). Further, the attachment means may include means for connecting the section 3 to lumen section 4 such that the section 3 is positioned in the same spatial plan, or a different spatial plane, as the curved section 2. To do so, the section 3 and section 4 may comprise a male and female mated arrangement, for example, that allows either section 3,4 to be inserted into one another or otherwise connected to one another such that the section 3 is in a desired spatial plane with respect to curved section 2.

In the embodiment depicted in FIG. 1A the section 3 is located at the proximal or "first" end of the catheter 1, and is configured on the catheter 1 so that the section 3 (i.e., passageway 3b) is substantially within the same spatial plane as the curve section 2 that is located at the distal, "second" or opposite end of the catheter 1 (i.e., sections 2 and 3 are aligned in the same plane). In the embodiment depicted in FIG. 1A, this "same" plane is the plane formed by the "x-y" axis, though the axes that form the plane in FIG. 1A are merely exemplary, it being understood that the axes may change depending on the position of the user that is inserting the catheter 1, and the position of the catheter 1.

In the embodiment depicted in FIG. 1A, the curve section 2 and section 3 are shown positioned in a "12 o'clock" position (i.e., pointing upwards toward the sky, or substantially perpendicular to a plane that contains the user's waistline, e.g., a plane formed by the "y-z" axes) in order to complete self-catheterization (i.e., the user or patient inserts the catheter 1 himself/herself).

Figure 1B:
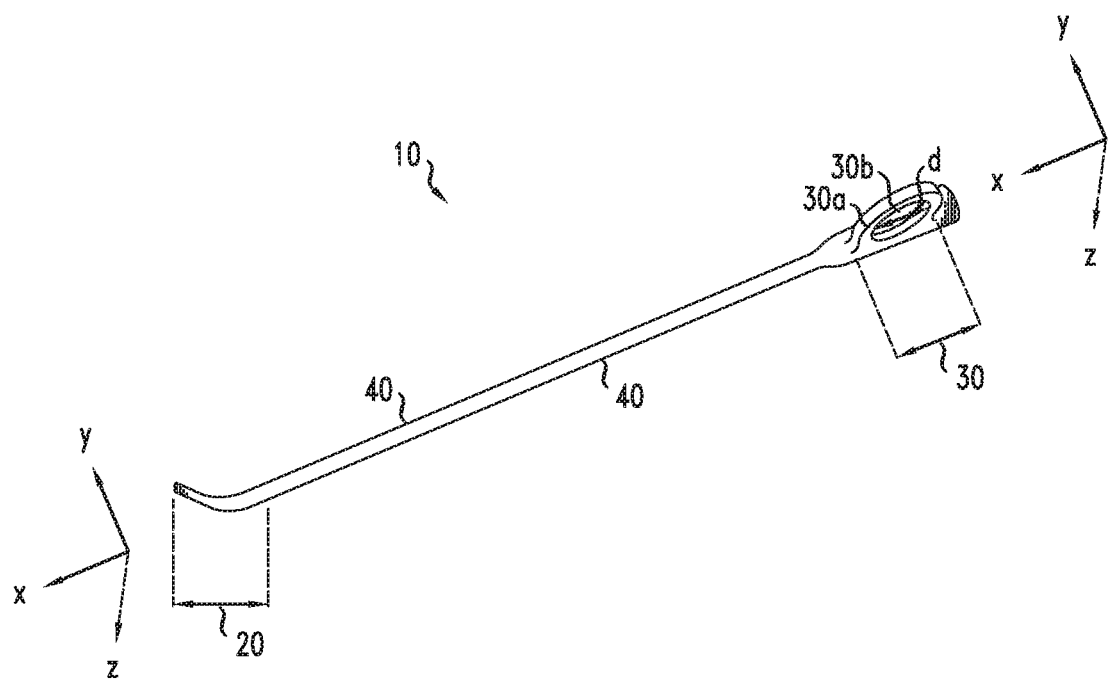
FIG. 1B depicts a rendering of another catheter according to another embodiment of the invention.

Referring now to FIG. 1B there is depicted an alternative embodiment of a catheter 10. As depicted, the catheter 10 may comprise an alignment indication section 30 comprising an open passageway 30b that is configured such that it is in a different spatial plane than the Coude curved section 20. In the embodiment depicted in FIG. 1B the section 30 (i.e., passageway 30b) is configured in a plane that is at a 90° angle (e.g., x-z) from the plane (x-y) that contains the curved section 20. It should be understood that this is just one of the angles that the indication section 30 may be configured in.

As configured in FIG. 1B, the catheter 10 may be more easily inserted into an individual by a care-giver, such as a nurse, physician's assistant or physician in order to provide the care-giver with spatial control when the individual is laying in a supine position on a hospital bed, for example, and the care-giver is positioned on the right side of the bed. Accordingly, the catheter 10 is may be used by a care-giver such that the curved section 20 is anteriorly positioned with respect to an individual in a supine position using the alignment indication section 30.

Though the catheter 10 is depicted as a one-piece device, it should be understood that this is exemplary. In an alternative embodiment, the section 30 may be a separate component that can be attached to the lumen section 40 of the catheter 10, for example, by attachment means that are known in the art (e.g., snap-on connections, threaded connections, mated, non-threaded connections). Further, the attachment means may include means for connecting the section 30 to lumen section 40 such that the section 30 is positioned in a different spatial plane, as the curved section 20. To do so, the section 30 and section 40 may comprise a male and female mated arrangement, for example, that allows either section 30,40 to be inserted into one another or otherwise connected to one another such that the section 30 is in a desired spatial plane with respect to curved section 20.

Still further, the alignment indication section 30 may be independently movable or rotatable with respect to an axis that contains lumen section 40 (the x-axis in FIG. 1B). That is, section 30 may rotate while section 40 does not.

For example, the section 30 may comprise a locking, rotating mechanism (not shown in figures) that allows the section 30 to be independently rotated with respect to lumen section 40 and then locked into a position with respect to an axis of lumen section 40 (and, unlocked to move the catheter 10 to a different position). Accordingly, the section 30 may be configured in the same plane as the curved section 20 when the catheter 10 is being used for self-catheterization, or be configured (i.e., moved or rotated) so that it is configured in a different plane as the curved section 20 when the catheter 10 is being inserted into an individual by a care-giver.

In one embodiment the diameter "d" of the passageways 3*b*,30*b* may be 1.9 centimeters which corresponds to the average anatomical size of a person's thumb, it being understood the diameter of the passageways 3*b*,30*b* may vary depending on the size of the user's finger or size of another type of insertion aid or tool. In an alternative embodiment, the passageways 3*b*,30*b* may comprise an adjustable loop section whose diameter may be adjusted to fit any number of potential users' thumbs, fingers or another insertion aid or tool.

As indicated previously, though the shape of the sections 3,30 is shown as a loop that is mostly circular or semi-circular, it should be understood that this is merely exemplary. That is, it should be understood that the sections 3,30 may be shaped in any number of different ways, provided, the shape allows insertion of an individual's finger(s) (e.g., thumb) or a similar man-made aid, tool or device. In alternative embodiments section 3,30 may be made from a flexible material that allows a top portion 3*a*,30*a* (when there is a top portion, i.e., top portion 3*a*, 30*a* may be removed) to be compressed. In other embodiments, the sections 3,30 may include indentations on the inside or outside of their circumferential surface for ease of holding and adjusting the position of the catheters 1,10.

In order for the Coude catheter 10 to be utilized correctly, its distal or curved end 20 must be oriented so that it is pointing anteriorly or toward the ceiling of the individual when the individual is in a supine position as the catheter 10 passes through the individual's prostatic urethra.

In both the configurations shown in FIGS. 1A and 1B, the catheters 1,10 comprise an alignment indication section 3,30 on their proximal end to allow proper drainage from an individual's bladder.

Figure 2:
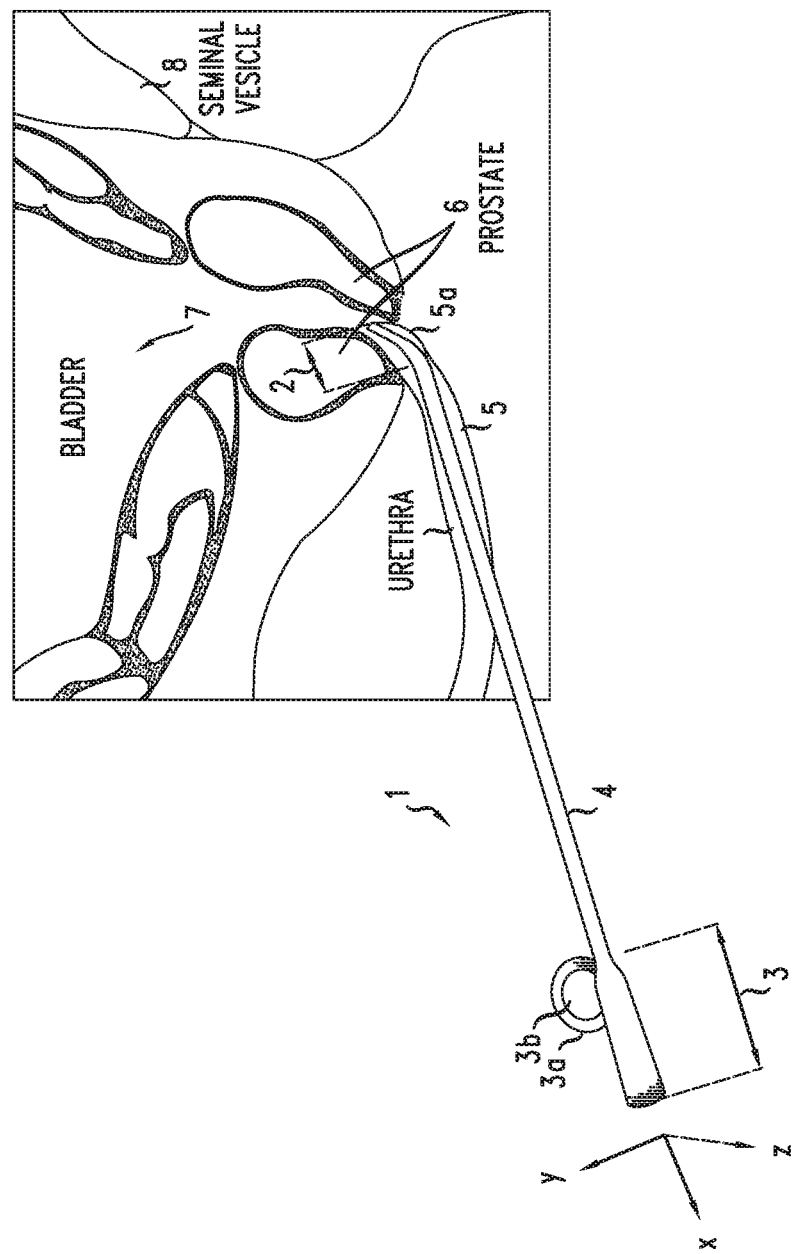
FIG. 2 depicts an illustration of the use of a catheter according to an embodiment of the invention.

Referring now to FIG. 2, there is depicted an illustration of one possible use of the inventive catheter 1 according to an embodiment of the invention that insures its distal or curved end 2 is always substantially oriented or positioned such that it is pointing anteriorly or toward the ceiling of the user when the user is in a supine position as the distal, curved end 2 of the catheter 1 reaches the prostatic urethra portion of the user.

As shown, the distal, Coude curved end section 2 of the catheter 1 is shaped so that it matches the shape of the prostatic urethra portion 5*a* of the user's urethra 5 passing through the user's prostate 6. Because the distal, curved end section 2 is so-shaped, it may pass through the portion 5*a* and prostate 6 on to the bladder 7 without harming the surrounding prostate 6, urethra 5 or other tissue 8. To allow the distal, curved end section 2 to effectively remove material from the bladder 7 it should be positioned within the correct spatial plane, otherwise the benefit of the shaped, curved catheter is lost, and in fact, could lead to injury. By configuring the section 3 and curved section 2 on the catheter 1 so that both sections 2,3 are within the same spatial plane for self-catheterization, the user is always aware of the position of the curved section 2 viz-a-viz his bladder even though the user cannot see the curved section 2—it is in the same plane as the section 3 that the user can see, feel and manipulate.

In the case where the section 3 (or 30 in FIG. 1B) is viewed by the user as being in the proper spatial plane, the position of the catheter 1 need not be adjusted. However, in the case where the position of the section 3 is in the improper spatial plane, the catheter may be adjusted (e.g., rotated) by an individual by, for example, placing the individuals fingers within the passageway 3*b* (or 30*b* in FIG. 1B) so that the section 3, and thus the curved section 2, are in the proper spatial plane.

The foregoing description only describes a few of the many possible embodiments of the invention. Numerous changes and modifications to the embodiments disclosed herein may be made without departing from the general spirit and scope of the invention, the metes and bounds of which are best defined by the claims that follow.

What is claimed is:

1. An integrated, one-piece urinary catheter configured for catheterization of unobstructed, narrowed and obstructed urethras ("urethra") comprising:
   a Coude curved section on a distal end of the catheter, a straight lumen section for transporting urinary fluid,
   a loop section extending from a proximal end of the catheter comprising an opening that is configured to permit insertion of a person's finger or fingers for adjusting a position of the Coude curved section on the distal end to permit proper passage of the Coude curved section through the urethra and to permit proper drainage of urine from a bladder for catheterization, wherein a cross section of the opening is further configured to remain substantially within a same spatial plane, including in the event of an obstruction, as the Coude curved section as the Coude curved section is adjusted for permitting proper drainage of the urine from the bladder for catheterization; and
   wherein the lumen section is configured between the curved section and the proximal end of the catheter and the Coude curved section, lumen section and loop section comprise an integrated, one-piece urinary catheter.

2. The catheter as in claim 1 wherein the catheter comprises a silicon or polyvinyl chloride catheter.

3. The catheter as in claim 1 wherein the loop section is configured in a semi-circular shape.

4. The catheter as in claim 1 wherein the opening is configured to have an inside diameter of approximately 1.9 millimeters.

5. The catheter as in claim 1 wherein a diameter of the opening is sized to allow different size fingers or a manipulative device to fit within the opening.

6. The catheter as in claim 1 wherein the loop section comprises a compressible top portion.

7. The catheter as in claim 1 wherein the loop section comprises one or more indentations on an inside or outside circumferential surface.

8. An integrated, one-piece urinary catheter configured for catheterization of unobstructed, narrowed and obstructed urethras ("urethra") comprising:
a Coude curved section on a distal end of the catheter, a straight lumen section for transporting urinary fluid,
a loop section extending from a proximal end of the catheter and comprising an opening, wherein a cross section of the opening is within a spatial plane that is not the same as, and not perpendicular to, a plane containing the Coude curved section prior to catheterization, and configured to permit insertion of a person's finger or fingers for adjusting a position of the Coude curved section on the distal end to permit proper passage of the curved section through the urethra and to permit proper drainage of urine from a bladder, wherein the loop section and the Coude curved section remain in their respective spatial planes including in the event of an obstruction; and
wherein the lumen section is configured between the curved section and the proximal end, and the Coude curved section, lumen section and loop section comprise an integrated, one-piece urinary catheter.

9. The catheter as in claim 8 wherein the loop section is configured in a semi-circular shape.

10. The catheter as in claim 8 wherein the loop section comprises a compressible top portion.

11. The catheter as in claim 8 wherein the loop section comprises one or more indentations on an inside or outside circumferential surface.

12. A method for catheterization of unobstructed, narrowed and obstructed urethras ("urethra") comprising:
inserting a Coude, curved section on a distal end of a one-piece, integrated urinary catheter into the urethra, and
positioning a loop section, that extends from a proximal end of the integrated catheter and that comprises an opening to permit insertion of a person's finger or fingers, for adjusting a position of the Coude curved section on the distal end to allow proper passage of the Coude curved section through the urethra and to permit proper drainage of urine from an individual's bladder for catheterization, wherein a cross section of the opening is further configured to remain substantially within a same spatial plane, including in the event of an obstruction, as the Coude curved section as the Coude curved section is adjusted for permitting proper drainage of the urine from the bladder for catheterization.

13. The method as in claim 12 further comprising orientating the curved section anteriorly with respect to a patient in a supine position using the loop section.

14. The method as in claim 12 further comprising attaching the loop section comprising the opening on the proximal end of the catheter.

15. A urinary catheter configured for catheterization of unobstructed, narrowed and obstructed urethras ("urethra") comprising:
a Coude curved section on a distal end of the catheter, a straight lumen section for transporting urinary fluid,
a loop section configured to attach to the lumen section and extending from a proximal end of the catheter comprising an opening that is configured to permit insertion of a person's finger or fingers and for adjusting a position of the Coude curved section on the distal end to permit proper passage of the Coude curved section through the urethra and to permit proper drainage of urine from a bladder for catheterization, wherein a cross section of the opening is further configured to remain substantially within a same spatial plane, including in the event of an obstruction, as the Coude curved section as the Coude curved section is adjusted for permitting proper drainage of the urine from the bladder for catheterization; and
wherein the lumen section is configured between the curved section and the proximal end of the catheter and the Coude curved section.

* * * * *